United States Patent [19]

Gaudiana et al.

[11] Patent Number: 4,503,248

[45] Date of Patent: Mar. 5, 1985

[54] SUBSTITUTED-QUATERPHENYLENE MONOMERS FOR THE PRODUCTION OF POLYAMIDES THEREFROM

[75] Inventors: Russell A. Gaudiana, Merrimack, N.H.; Palaiyur S. Kalyanaraman, Chalfont, Pa.

[73] Assignee: Polaroid Corporation, Cambridge, Mass.

[21] Appl. No.: 498,984

[22] Filed: May 27, 1983

Related U.S. Application Data

[62] Division of Ser. No. 239,180, Mar. 2, 1981, Pat. No. 4,393,194.

[51] Int. Cl.³ .............................................. C07C 87/00
[52] U.S. Cl. .................................... 564/307; 564/305; 564/441; 564/442; 568/585; 568/586; 568/931
[58] Field of Search ............... 564/305, 441, 442, 307; 568/585, 586, 931

[56] References Cited

PUBLICATIONS

Chem. Abs. 62, 646c, (1965), Wirth, "Synthesis and Properties of a Nitro Poly-p-phenylene and of Nitro p-oligophenylenes".
Chem. Abs., Seventh Formula Index, p. 5182F.

Primary Examiner—Thomas A. Waltz
Assistant Examiner—H. B. Shubin
Attorney, Agent, or Firm—Louis G. Xiarhos

[57] ABSTRACT

A class of polyamides comprising recurring units having substituted-quaterphenylene radicals is disclosed. The polymers comprise recurring units of the formula

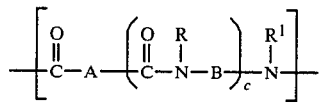

wherein each of A and B is a divalent radical, except that B can represent a single bond; R and $R^1$ are each hydrogen, alkyl, aryl, alkaryl or aralkyl; and c is zero or one; and wherein, when c is one, at least one of A and B is a substituted-quaterphenylene radical having the formula

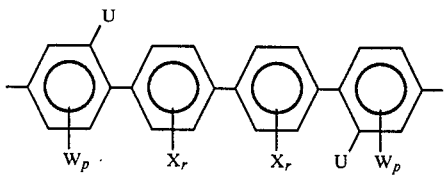

where each U is a substituent other than hydrogen, each W is hydrogen or a substituent other than hydrogen, each p is an integer from 1 to 3, each X is hydrogen or a substituent other than hydrogen and each r is an integer from 1 to 4, the U, $W_p$ and $X_r$ substitution being sufficient to provide the radical with a non-coplanar molecular configuration; and wherein, when c is zero, A is a substituted-quaterphenylene radical as aforedescribed.

The polyamide materials exhibit solubility in select solvents including those of the non-amide type and are characterized by high electron density substantially cylindrically distributed about the long axis thereof. The molecularly oriented polymers are optically uniaxial and are suited to application in optical filter and other devices where a highly refractive and birefringent polymeric material is desired.

3 Claims, 5 Drawing Figures

SUBSTITUTED-QUATERPHENYLENE MONOMERS FOR THE PRODUCTION OF POLYAMIDES THEREFROM

This is a division of application Ser. No. 239,180, filed Mar. 2, 1981, now U.S. Pat. No. 4,393,194.

BACKGROUND OF THE INVENTION

This invention relates to a novel class of polymers exhibiting optically anisotropic properties. More particularly, it relates to a class of substituted-quaterphenylene polyamides having a highly birefringent character.

Materials having a birefringent character have been variously applied in connection with the construction of filter and other optical devices. Frequently, a birefringent element utilized in an optical filter or other device will comprise a plate made from a monocrystalline form of birefringent optical material. Single crystals are expensive materials and are not readily formed to the desired shape or conformation required in particular applications. The size to which such crystals can be grown represents an additional limitation on the utilization of such materials in optical devices.

Optical devices including a birefringent material in the form of a polymeric layer, such as may be formed by the unidirectional stretching of a suitable polymeric material, have also been described. Thus, light-polarizing devices utilizing a polymeric birefringent layer have been described in U.S. Pat. No. 3,213,753 (issued Oct. 26, 1965 to H. G. Rogers). Optical devices including polymeric birefringent materials have also been set forth, for example, in U.S. Pat. No. 3,506,333 (issued Apr. 14, 1970 to E. H. Land) and in U.S. Pat. No. 3,610,729 (issued Oct. 15, 1971 to H. G. Rogers). Frequently, the efficiency of an optical filter, polarizing or other optical device including a birefringent element or layer will depend upon the realization of large net differences in refractive index between a birefringent material and adjacent or contiguous materials. In general, such net differences will be maximized where a birefringent material is highly birefringent. Correspondingly, large net differences in refractive indices of contiguous materials will be unattainable where birefringent polymeric materials otherwise suited to application in an optical device tend to exhibit either low or only marginal birefringent character. Accordingly, polymeric materials exhibiting a highly birefringent character will be of particular interest for optical applications and enhanced efficiency.

SUMMARY OF THE INVENTION

The present invention provides a class of polymeric materials exhibiting high birefringence and is based in part upon the discovery that the incorporation into a polyamide of certain divalent substituted-quaterphenylene radicals, in the form of substituted-quaterphenylene radicals having the phenylene moieties thereof in a non-coplanar molecular configuration, imparts to the polyamide material an unusually high anisotropic or birefringent character. Transparent polymeric materials exhibiting uniaxial optical properties, i.e., only two indices of refraction, and which exhibit solubility in organic solvents are provided by the polymers of the present invention. These polymers comprise certain repeating or recurring units in chain-extended relation, the recurring units including divalent substituted quaterphenylene radicals. The presence of substituent groups on the phenylene moieties of the recurring units such that the phenylene moieties thereof are in a non-coplanar molecular configuration permits the provision of a substantially cylindrical distribution of electron density about the long axis of the polymer and the realization of high birefringence. There is thus simulated in a polymeric material optical properties of a uniaxial crystal. The present invention, thus, provides a class of polymers comprising recurring units of the formula

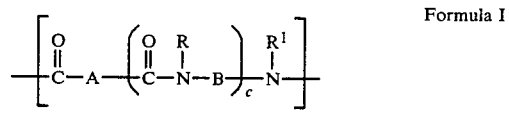

Formula I wherein each of A and B is a divalent radical, except that B can additionally represent a single bond; R and $R^1$ are each hydrogen, alkyl (e.g. methyl, ethyl), aryl (e.g., phenyl, naphthyl), alkaryl (e.g., tolyl), or aralkyl, e.g., benzyl); and c is zero or one; and wherein, when c is one, at least one of A and B is a substituted-quaterphenylene radical having the formula:

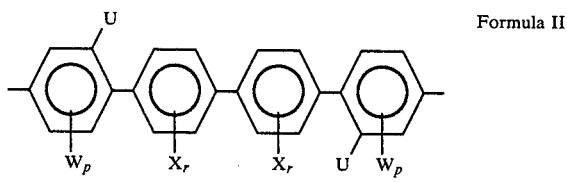

Formula II where each U is a substituent other than hydrogen, each W is hydrogen or a substituent other than hydrogen, each p is an integer from 1 to 3, each X is hydrogen or a substituent other than hydrogen and each r is an integer from 1 to 4, said U, $W_p$ and $X_r$ substitution being sufficient to provide said radical with a non-coplanar molecular configuration;
and wherein, when c is zero, A is a substituted quaterphenylene radical having the aforesaid formula.

According to another composition aspect of the present invention there are provided novel monomers of the formulae

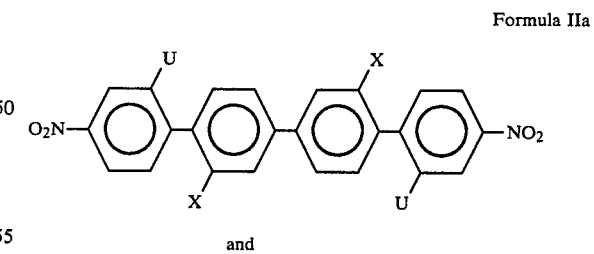

Formula IIa and

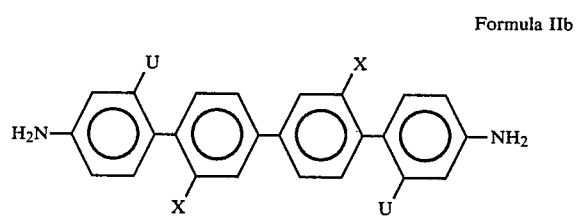

Formula IIb wherein each of U and X is halo (e.g., fluoro, bromo, chloro, iodo); nitro; alkoxy (e.g., methoxy); or substituted-alkyl (e.g., trifluoromethyl). Preferably, each U and X substituent is the same and is trifluoromethyl. The novel monomers are useful in the production of the novel polymers of the present invention.

THE DRAWINGS

DETAILED DESCRIPTION OF THE INVENTION

As described hereinbefore, the substituted-quaterphenylene polyamides of the present invention comprise recurring units of the formula

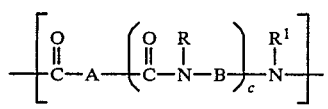

Formula I wherein c is zero or one and wherein A (when c is zero) or at least one of A and B (when c is one) comprises a divalent substituted-quaterphenylene radical as represented by the structure of Formula II hereinbefore. Thus, when c is zero, divalent radical A comprises a substituted-quaterphenylene radical having a non-coplanar molecular configuration. Similarly, when c is the integer one, one or both of divalent radicals A and B comprises such a substituted-quaterphenylene radical. It is preferred from the standpoint of ease of preparation that each of R and $R^1$ be hydrogen, although each of R and $R^1$ can be alkyl, aryl, alkaryl or aralkyl.

The molecularly oriented and highly birefringent polymers of the present invention comprise repeating molecular units represented by the structure of Formula I. These units exhibit high electron density substantially cylindrically distributed about the long axis thereof. The optically uniaxial character of the molecularly oriented substituted-quaterphenylene polyamides of the present invention is importantly related to the molecular configuration or structure of the substituted-quaterphenylene repeating units of the polymer and to the distribution of electron density. The presence of substituent groups on the phenylene moieties of the quaterphenylene radicals such that the phenylene moieties are in a non-coplanar relation to one another so as to provide a substantially cylindrical distribution of electron density about the long axis of the polymer and the recurring units thereof permits the realization of high birefringence and the simulation in a polymeric material of optical properties of a uniaxial crystal.

The birefringence of oriented polymers of the present invention can be represented in relation to molecular configuration and electron density distribution according to a dimensionless geometric index G set forth by the relationship:

$$G = 0.222 \times E \times (L/D)$$

wherein E is a dimensionless eccentricity factor defined by the relationship $$E = (1+e_L)/(1+e_T)$$

where $e_L$ is the longitudinal eccentricity of the polarizability of the repeating molecular unit and $e_T$ is the transverse eccentricity of the electron polarizability of the repeating molecular unit, L is the length of the repeating molecular unit along the main axis thereof and D is the mean diameter of the repeating molecular unit. The contribution to birefringence of the molecular structure of a repeating, chain-extending unit and of electron density distribution will be better understood by reference to the drawings hereof.

Figure 2:
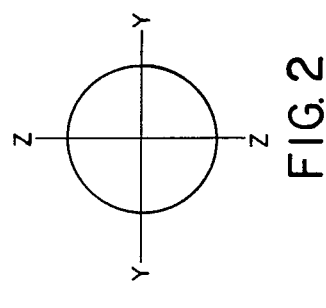
FIG. 2 is a cross-sectional view along the line 1—1 of FIG. 2.
Figure 1:
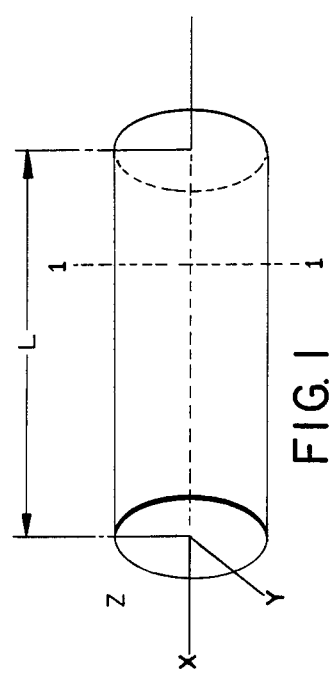
FIG. 1 is a geometric representation of molecular dimensions of a repeat unit of a polymeric material of the invention.

In FIG. 1 is shown a geometrical representation of a repeating chain-extending molecular unit of a polymeric material of the present invention. Each repeating unit may thus be visualized as a repeating rod-like segment of finite length L, and of a generally cylindrical configuration. Birefringence has been found to be importantly related to the molecular structure of the repeating units of the polymer in accordance with the relationship of geometric index G, set forth hereinbefore. A highly birefringent polymeric material of the invention will thus comprise a plurality of molecular units in chain-extended relationship, each unit having a length L, shown in FIG. 1. The long axis X of each repeating unit forms, in the chain-extended polymer, the long axis or backbone. Each axis in FIG. 1 forms a right angle with respect to any other axis. The mean diameter D, set forth in the geometric index G, is determined for each repeating unit by the expression $D=(Y+Z)/2$. In FIG. 2 is shown along line 1—1 of FIG. 1, a cross-sectional view. The shown Y and Z axes are at right angles to one another, the X axis comprising the axis of the cylinder extending in a direction normal to the plane of the paper.

Figure 4B:
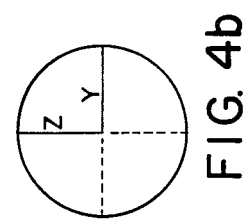
FIGS. 4a and 4b show, respectively, ellipsoidal and circular cross-sectional distribution of electron density about the long axis of a recurring unit of a polymeric material of the invention.
Figure 4A:
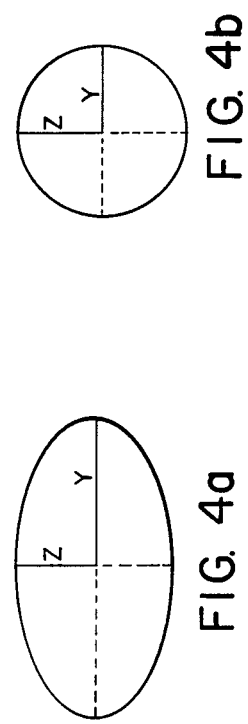
Figure 3:
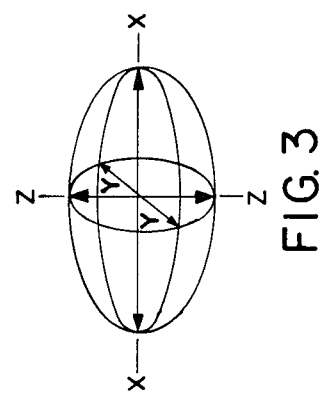
FIG. 3 is a vectorial representation of bond and group polarizabilities of a repeat unit of a polymeric material of the invention.

In addition to a rigid rod-like geometry in a polymeric material as the result of an end-to-end combination of repeating units hereof, the electron density distributed around the long axis of the polymer, variously treated as a cylindrical or ellipsoidal distribution, is believed to comprise a major contributing factor to optical anisotropy or birefringence. High electron density substantially cylindrically distributed around the long axis of a polymer is exhibited in a polymer of coaxially-bonded repeating units comprising non-coplanar, particularly orthogonal, substituted-quaterphenylene radicals. An orthogonal relationship between adjacent phenylene rings can be nearly attained by the placement of substituents with large steric effects on at least one ortho-position of next adjacent phenylene rings. In FIG. 3 is shown a vectorial representation of bond and group polarizabilities of a repeating unit of a polymer of the invention. It will be appreciated that electron density distribution about axis X will be variously treated as a cylindrical or ellipsoidal distribution depending upon the relative magnitudes of the Y and Z vectors. In FIG. 4a is shown an ellipsoidal cross-section along the axis of FIG. 3 where the magnitude of the shown Y vector is greater than that of the Z vector. Ideally, Y and Z vectors would be equal and the resulting circular cross-sectional distribution along the X axis is shown in FIG. 4b.

By a combination of longitudinal eccentricity ($e_L$) and transverse eccentricity ($e_T$), based upon bond and group polarizabilities, and the length and mean diameter of a repeating unit, a geometric index, G, related to optical anisotropy or birefringence, can be represented as follows:

$$G = 0.222 \left( \frac{1 + e_L}{1 + e_T} \right) \frac{L}{D}$$

wherein $e_L$, $e_T$, L and D have the meanings hereinbefore ascribed. Longitudinal eccentricity $e_L$ may be represented according to the following relationship $$e_L = \frac{\sqrt{X^2 - \left( \frac{Y + Z^2}{2} \right)}}{X}$$

Transverse eccentricity $e_T$ may be represented by the relationship $$e_T = \frac{\sqrt{Y^2 - Z^2}}{Y}$$

wherein the magnitude of vector Y is the larger of the Y and Z vectors. Ideally, transverse eccentricity $e_T$ will equal zero and longitudinally eccentricity $e_L$ will equal one, in which case, the eccentricity factor, E, will equal the theoretical maximum of two.

Geometric index G can be calculated for repeating units of a polymer of the present invention by resort to mean diameter and length values and longitudinal and transverse eccentricity values calculated from experimentally determined dihedral angles. It will be appreciated that the magnitude of values of length, mean diameter, longitudinal eccentricity and transverse eccentricity will materially influence the value of geometric index G. Thus, it will be appreciated that a repeating unit having, for example, a length of about twice that of a repeating unit having a different molecular structure and configuration will have a geometric index of about twice that of such different repeating unit. Accordingly, in making comparisons of geometric indices and magnitude thereof in relation to structural differences between comparative molecular repeating units, such differences in length should be borne in mind.

In general, experimentally determined birefringence values of materials comprised of repeating units as aforedescribed, will correlate directionally with values of geometric index, G, of the repeating units. Thus, recurring units having higher geometric index values will, in general, provide polymers exhibiting higher birefringence. Polymeric materials comprised of repeating units as aforedescribed, depending upon the nature of substituent groups and the influence thereof on electron density distribution, will generally be comprised of repeating units having a geometric index value, G, of about 0.8 or higher. It will be preferred, however, that polymeric materials hereof comprise repeating units having geometric index values of one or higher. Especially preferred herein are polymers comprising repeating units of geometric index value of 1.2 or higher.

High birefringence observed in the case of substituted-quaterphenylene polyamides comprised of recurring units of high geometric index value (G) is believed to be importantly related to the presence in such units of the inter-bonded phenylene rings where the phenylene rings are in twisted relation to one another, i.e., where the phenylene rings are in non-coplanar molecular configuration with respect to each other or, preferably, in mutually orthogonal planes. It has been found that the presence of substituent moieties on interbonded phenylene rings, of type and position such as to effect a non-coplanar molecular configuration with respect to the interbonded phenylene rings, provides a recurring unit having a high geometric index. The condition of non-coplanarity among phenylene rings in a recurring unit, or presence in such units of rings in "twisted" configuration relative to one another has been found to be importantly related to high birefringence in the rigid rod-like oriented polymers resulting from the end-to-end joining of such recurring units.

As described hereinbefore, substituted-quaterphenylene polyamides of the present invention include those comprising recurring units of the formula

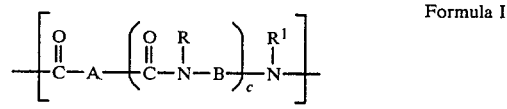

Formula I wherein c is zero or one. It will be appreciated that polyamides comprising the following recurring units are contemplated when c is one:

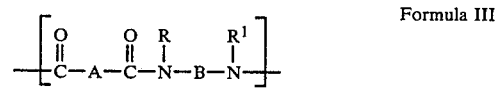

Formula III

In such recurring units, at least one of divalent radicals A and B will comprise a substituted-quaterphenylene radical of non-coplanar molecular configuration conforming to the formula:

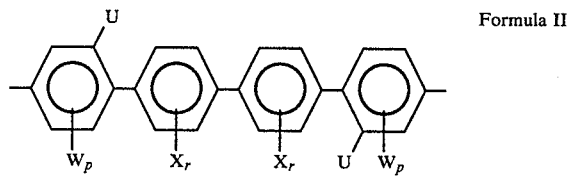

Formula II

In substituted-quaterphenyl radicals A and/or B of the type represented by Formula II, each U will comprise a substituent other than hydrogen; each W will comprise hydrogen or a substituent other than hydrogen; and each p will be an integer of from 1 to 3. In the case of such radicals, each X will be hydrogen or a substituent other than hydrogen and each r will be an integer of from 1 to 4. It will be appreciated from the nature of U, W, p, X and r, as set forth, that at least two aromatic nuclei of the quaterphenylene radical represented by Formula II will be substituted by a moiety other than hydrogen and that each substituent, U, will be positioned in an ortho relationship to bridging carbon atoms of the quaterphenylene nuclei. Preferably, each aromatic nucleus of the quaterphenylene radical of Formula II will contain a substituent other than hydrogen positioned in an ortho relationship to the bridging carbon atom of a next-adjacent phenylene nucleus such that the divalent radical has the following formula Formula IV

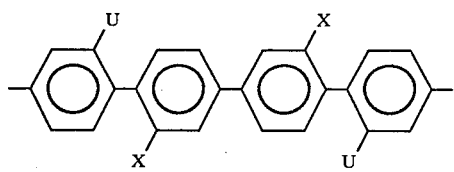

wherein each of U and X comprises a substituent other than hydrogen.

The nature and positioning of substituents U, W, and X of the quaterphenylene radical of Formula II can vary widely, consistent with the provision of a quaterphenylene radical having a non-coplanar molecular configuration. As used herein, the term non-coplanar molecular configuration refers to a molecular configuration whereby the substituted interbonded aromatic nuclei are in different planes.

While applicants do not wish to be bound by precise theory or mechanism in explanation of the highly birefringent character observed in oriented polymers comprising recurring units of high geometric index, it is believed that the non-coplanar character conferred or promoted by the presence of substituents in the aforedescribed recurring units provides a distribution of high electron density cylindrically about the long axis of the polymer and that this distribution at least in part contributes to unusually high birefringence observed in such polymers.

The nature of substituency U, Wp and Xr should be such as to provide the quaterphenylene radical of formula II with a non-coplanar molecular configuration referred to hereinbefore. Such configuration will in part be determined by the positioning and size of non-hydrogen substituents on the aromatic nuclei of the quaterphenylene radical and upon the number of such substituents on such aromatic nuclei. For example, where the quaterphenylene radical contains only two non-hydrogen substituents, i.e., two U substituents, the nature and, in particular the size of such U substituents, should be such as to provide the desired non-coplanar molecular configuration. Suitable U substituents herein include halogen (e.g., fluoro, chloro, bromo, iodo); nitro; alkyl (e.g., methyl, ethyl); alkoxy (e.g., methoxy); substituted-alkyl (e.g., trifluoromethyl or hydroxyalkyl); cyano; hydroxy; thioalkyl (e.g., thiomethyl); carboxy; sulfonic acid esters; sulfinic acid esters; carboxyamide; sulfonamide; amino; and carbonyl. Substituent X can comprise hydrogen or any of the substituents set forth in connection with substituent U. Preferably, at least one X substituent will comprise a substituent other than hydrogen. Each substituent W can comprise hydrogen or a substituent other than hydrogen as set forth in connection with substituents U and X. Preferably, each W will be hydrogen and p will be the integer three.

Preferred substituted-quarterphenylene polyamides herein are those comprising recurring units having the quaterphenylene radical of Formula IV.

Formula IV

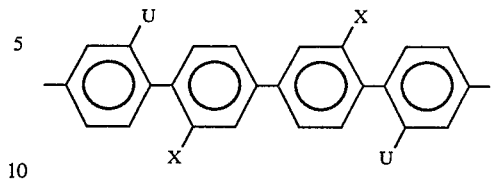

wherein each of U and X is a substituent other than hydrogen. The presence of such non-hydrogen substituents on each of the aromatic nuclei of the radical promotes a condition of non-coplanarity. Examples of such preferred substituents, which may be the same or different, include halo, nitro, alkoxy and trifluoromethyl. While the presence of such non-hydrogen substituents is preferred from the standpoint of promoting non-coplanarity, it will be appreciated from the nature of substituents W and X set forth in connection with Formula II hereinbefore, that each X and W can be hydrogen and that, accordingly, substituent U will in such instance desirably comprise a bulky substituent such as will provide steric hindrance to a condition of coplanarity.

Where only one of said A and B radicals is a substituted quaterphenylene radical conforming to the radical represented by the structure of Formula II, the remaining A or B radical can comprise any of a variety of divalent radicals so long as the birefringent properties of the polyamide material are not effectively negated. In general, where only one of the A and B radicals conforms to the structure represented by Formula II, the remaining A or B radical will desirably be a divalent radical which does not confer transverse eccentricity to the recurring unit. Similarly, where one of radicals A or B is a radical which confers transverse eccentricity to the recurring unit, the other of radical A or B will desirably be a radical which confers high longitudinal eccentricity such that the recurring unit of the polymer exhibits a high geometric index.

When only one of radicals A and B is a substituted-quaterphenylene radical, the other of A or B can be any of a variety of divalent radicals including, for example, unsubstituted biphenylene or stilbene radicals; phenylene; transvinylene; or ethynylene. Also suitable are polyunsaturated divalent radicals conforming to the formula

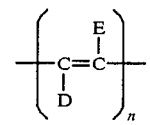

where n is an integer of at least two (e.g., two or three) and each of D and E is hydrogen or alkyl (e.g., methyl) and inclusive of such polyunsaturated divalent radicals as trans-trans-1,4-butadienylene, i.e.,

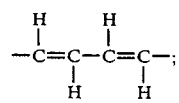

and 1,4-dimethyl-trans-trans-1,4-butadienylene, i.e.,

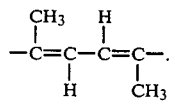

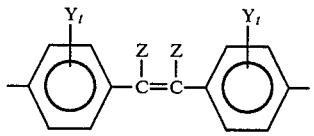
Formula VI

It will be appreciated that compounds having amino groups directly attached to carbon atoms having linear unsaturation are not stable and that, accordingly, the aforesaid vinylene, ethynylene and butadienylene radicals cannot serve as B radicals in the recurring units represented by the structure of Formula III.

Where only one of radicals A and B is a substituted-quaterphenyl radical of Formula II the other of A or B can be a radical which does not conform to the structure of Formula II but which has a non-coplanar molecular configuration and a substantially cylindrical distribution of electron density about the long axis thereof. Suitable radicals, polymers containing same and methods for their preparation are described in the U.S. patent application of H. G. Rogers et al., Ser. No. 239,069, issued May 17, 1983 as U.S. Pat. No. 4,384,107. Examples of such radicals include divalent substituted-biphenyl radicals of the formula

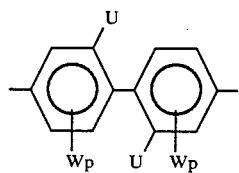
Formula V where U, W and p have the meanings described herein and the U and Wp substitution is sufficient to provide the radical with a non-coplanar molecular configuration; and divalent substituted-stilbene radicals of the formula where each of Y and Z is hydrogen or a substituent other than hydrogen, as described herein, and each t is an integer from 1 to 4, with the proviso that when each said Z is hydrogen, at least one said Y substituent is a substituent other than hydrogen positioned on the corresponding nucleus ortho with respect to the

moiety of said radical, the Z and $Y_t$ substitution being sufficient to provide said radical with a non-coplanar molecular configuration.

In general, from the standpoint of maximized birefringent properties, it will be preferred that each of radicals A and B comprise a divalent substituted-quaterphenylene radical exhibiting a non-coplanar molecular configuration and conforming to the structure of Formula II. It will be appreciated, however, that the particular nature of such A and B radicals may affect the ability to readily orient the polyamides as by extrusion, stretching or the like. Accordingly, where the ability of a polyamide material to be oriented is effectively reduced by the presence in the polyamide of each of radicals A and B of non-coplanar molecular configuration and conforming to the structure of Formula II, it will be preferred that only one of such radicals A and B of the polyamide material conform to the structure thereof.

Inclusive of substituted-quaterphenylene polyamides of the present invention represented by the structure of Formula III are those having recurring units represented by the following structures wherein, unless otherwise specified, U, W, p, X and r have the meanings set forth hereinbefore:

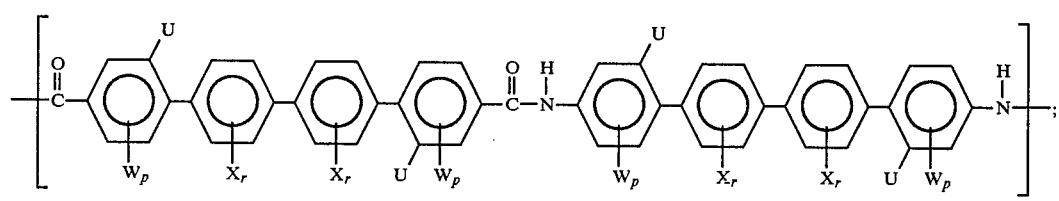
Formula VII

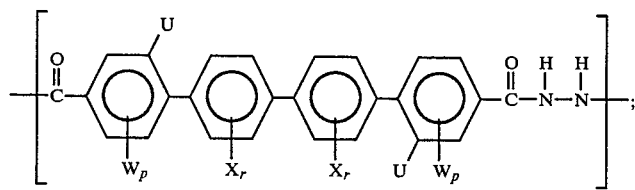
Formula VIII

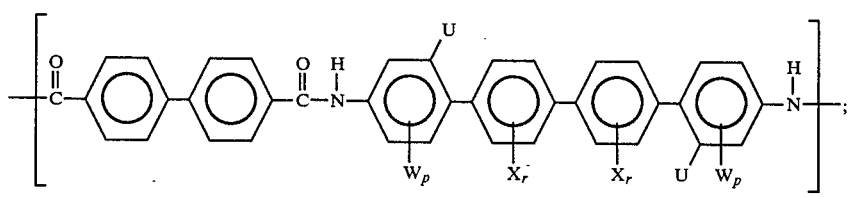
Formula IX

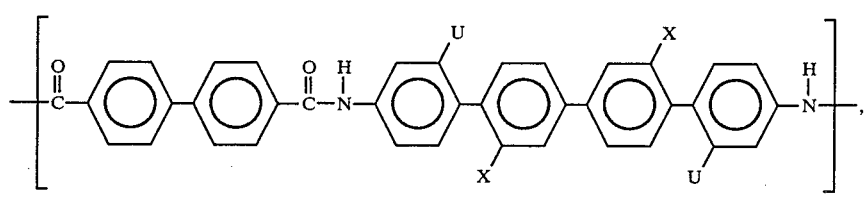

Formula X where each X is other than hydrogen;

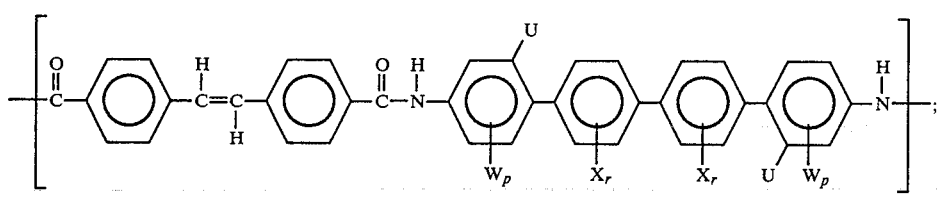

Formula XI

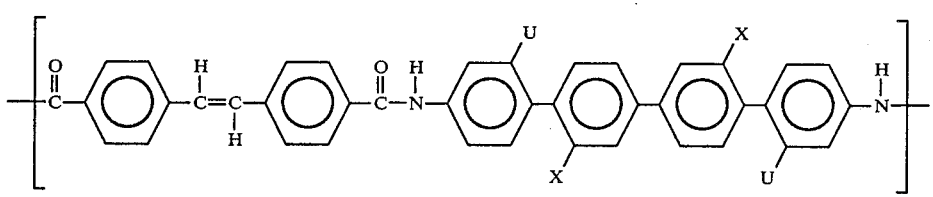

FORMULA XII where each X is other than hydrogen;

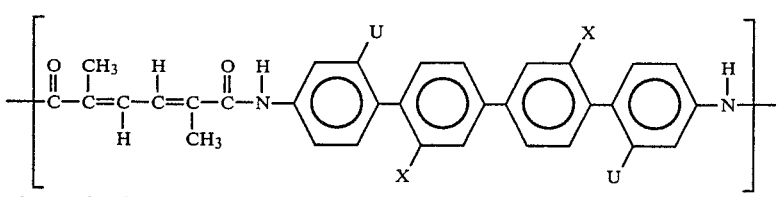

FORMULA XIII where each X is other than hydrogen;

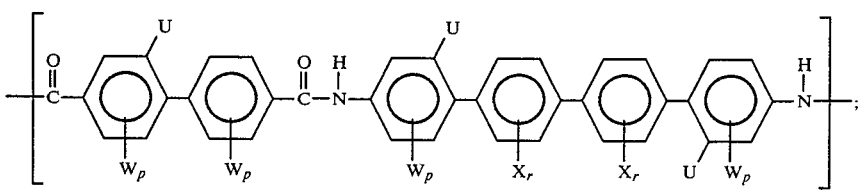

FORMULA XIV

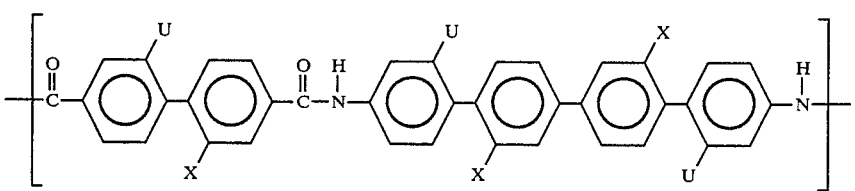

FORMULA XV where each X is other than hydrogen.

From inspection of the general formula set forth as descriptive of recurring units of the substituted-quaterphenylene polyamides, i.e., recurring units of the formula

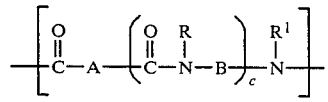

Formula I it will be appreciated that, when c is zero, the recurring units will be represented by the following formula:

Formula XVI

In such recurring units, radical A will comprise a divalent substituted-quaterphenyl radical having a non-coplanar molecular configuration and conforming to the structure of Formula II set forth hereinbefore, i.e.,

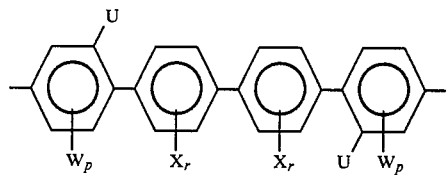

Formula II where U, W, p, X and r have the same meanings.

Inclusive of polyamides represented by the structure of Formula XVI are those having recurring units represented by the following structures wherein U, W, p, X and r, unless otherwise indicated, have the meanings set forth hereinbefore:

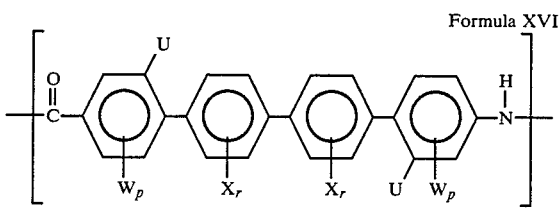

Formula XVII

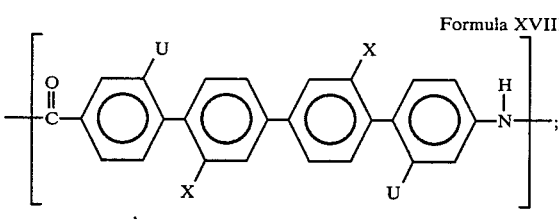

Formula XVIII where each X is other than hydrogen.

While the substituted-quaterphenylene polyamides described heretofore consist essentially of recurring units represented by the structures of Formulas III and XVI, i.e., recurring units of the formulas

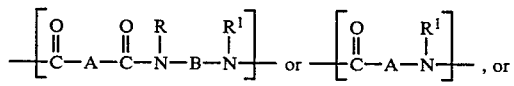

a combination of such recurring units, the substituted-quaterphenylene polyamides can also comprise recurring units not conforming to the described structures of Formulas III and XIV. Examples of recurring units which do not conform to such descriptions and which can be present in such polyamides in proportions which do not undesirably reduce the high birefringence of the polymeric material include, for example, recurring units having the formulas

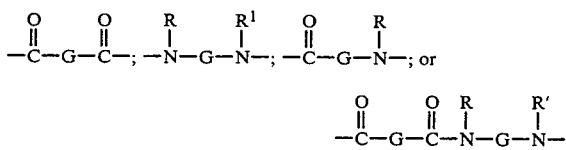

wherein G is a divalent radical such as 1,4-phenylene; 4,4'-biphenylene; vinylene; trans,trans-1,4-dimethyl-trans,trans-1,4-butadienylene; 2,4'-trans-vinylenephenylene; trans,trans-4,4'-bicyclohexylene, 2,5,7-bicyclooctatriene-1,4-, i.e.,

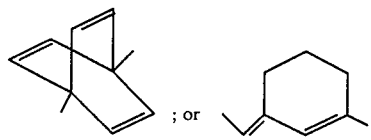

Divalent radical G can also comprise substituted biphenylene and stilbene radicals having a non-coplanar molecular configuration and a substantially cylindrical distribution of electron density about the long axis thereof. Suitable radicals, set forth herein in Formulas V and VI, are described in detail in the aforementioned U.S. Pat. No. 4,384,107. Other divalent radicals can, however, serve as radical G provided that such radicals do not adversely and materially reduce the birefringence of the polyamide material. It will be appreciated that G cannot represent an aliphatic unsaturated moiety where such moiety is to be bonded between two amino groups.

The substituted-quaterphenylene polyamides of the present invention can be prepared by resort to polyamide synthesis routes involving the polymerization of suitable acid halide and amine monomers in an organic solvent which may contain a solubilizing agent such as lithium chloride or chain-terminating agent where desired. Polyamides of the type represented by the structure of Formula I can be prepared, for example, by the reaction of a dicarboxylic acid halide of the formula

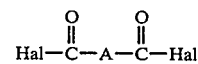

with a diamine of the formula

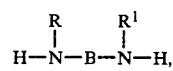

where Hal represents halogen, such as chloro or bromo and A and B have the meanings hereinbefore set forth, except that B cannot represent an aliphatic unsaturated moiety. Where B desirably represents a single bond in the polymers hereof, the aforesaid dicarboxylic acid halide of the formula

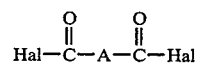

can be suitably reacted with hydrazine. The polymers of the present invention can be prepared in an organic solvent such as N-methyl pyrrolidone (NMP), tetramethylurea (TMU) or a mixture thereof, and preferably, in the presence of a salt such as lithium chloride to assist in the solubilization of reactant monomers and maintenance of a fluid reaction mixture. The preparation of a substituted-quaterphenylene polyamide of the present invention can be illustrated by reference to the preparation of poly[2,2',3'',2'''-tetrakis(trifluoromethyl)-1,1':4',1'':4'',1''':4'''-quaterphenylene]-trans-p,p'-stilbenedicarboxamide, a preferred polyamide herein, in accordance with the following reaction scheme:

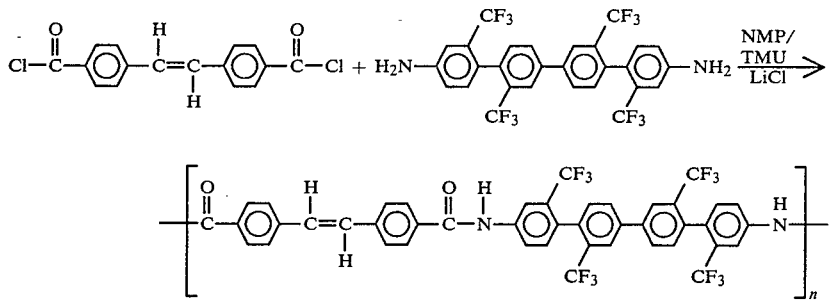

Substituted-quaterphenylene polyamides containing recurring units having the structure represented by Formula XVI,

can be prepared, for example, by the polymerization of a p-amino-quateraroyl halide monomer in the form of a halide, arylsulfonate, alkylsulfonate, acid sulfonate, sulfate or other salt. This polymerization can be illustrated by reference to the preparation of poly[2,2′,3″,2‴-tetrakis(trifluoromethyl)-1,1′:4′,1″:4″,1‴-quaterphenylene]carboxamide in accordance with the following reaction scheme showing the polymerization of the corresponding hydrochloride monomeric salt:

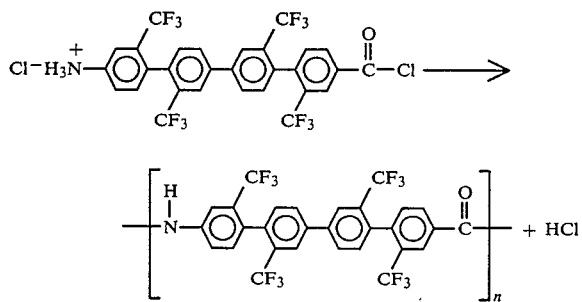

The substituted-quaterphenylene polyamides of the present invention can be prepared by polymerization of correspondingly substituted monomers in a suitable organic reaction solvent. Such solvents include amide and urea solvents including N-methyl-pyrrolidone and N,N,N′N′-tetramethylurea. Other suitable reaction solvent materials include tetrahydrofuran; N-methylpiperidone-2; N,N-dimethylpropionamide; N-methylcaprolactam; N,N-dimethylacetamide; hexamethylphosphoramide; and N,N′-dimethylethylene urea. The polymerization can be conducted by dissolving the monomer or monomers to be polymerized in the reaction solvent and allowing the exothermic polymerization reaction to occur usually with the aid of external cooling. In general, the polymerization will be conducted initially at a temperature of from about $-20°$ C. to about $15°$ C., and preferably, in the range of from about $-5°$ C. to about $5°$ C. Thereafter, usually within about one-half hour to one hour, the reaction will be heated with formation of a thickened polymeric mass of gel-like consistency. In general, the polymerization reaction will be conducted over a period of from about 1 to 24 hours, preferably, for about 3 to 18 hours.

While the monomer or monomers to be polymerized can be dissolved in a suitable amide or urea solvent and allowed to react with formation of the desired polymeric material, a preferred reaction sequence where a mixture of copolymerizable monomers is utilized involves the preparation of a solution of a first monomer in the amide or urea solvent and the addition thereto of a second or other monomer or a solution thereof in a suitable organic solvent therefor, such as tetrahydrofuran. External cooling of the resulting reaction mixture provides the desired substituted-quaterphenylene polyamide material in high molecular weight and minimizes the production of undesired side reactions or by-products.

The substituted-quaterphenylene polyamide materials prepared as described can be recovered by combining the polymerization reaction mixture with a non-solvent for the polymer and separating the polymer as by filtration. This can be effectively accomplished by blending the polymerization mixture with water and filtering the solid polyamide material. The polyamide can be washed with an organic solvent such as diethylether or a lower alkanol such as ethanol and dried, for example, in a vacuum oven.

Starting materials useful in the manufacture of substituted-quaterphenylene polyamides of the invention can be prepared by resort to a variety of organic synthetic routes. Preferred polyamides of the invention can be prepared, for example, by reaction of terephthaloyl chloride and/or trans-p,p′-stilbene dicarbonyl chloride with the diamino compound, 4,4‴-diamino-2,2′,3″,2‴-tetrakis(trifluoromethyl)-1,1′:4′,1‴-quaterphenyl. This novel diamine can be prepared, for example, from 2-bromo-5-nitro-benzotrifluoride by resort to the following reactions: (a) an Ullmann coupling of 2-bromo-5-nitrobenzotrifluoride utilizing active copper and dimethylformamide to provide 2,2′-bis-(trifluoromethyl)-4,4′-dinitro-1,1′-biphenyl; (b) a partial reduction utilizing aqueous sodium hydrosulfide to 4-amino-2,2′-bis-(trifluoromethyl)-4′-nitro-1,1′-biphenyl; (c) a diazotization of the resulting amine utilizing aqueous sodium nitrite and hydrochloric acid and a Sandmeyer reaction of the resulting diazonium salt with potassium iodide to provide 2,2′-bis-(trifluoromethyl)-4-iodo-4′-nitro-1,1′-biphenyl; (d) an Ullmann coupling of the resulting biphenyl compound utilizing active copper for production of 4,4‴-dinitro-2,2′,3″,2‴-tetrakis-(trifluoromethyl)-1,1′:4′,1″:4″,1‴-quaterphenyl; and (e) a reduction utilizing stannous chloride and hydrochloric acid for production of the desired diamine starting material. The production of this diamine starting material is illustrated by the following reaction sequence:

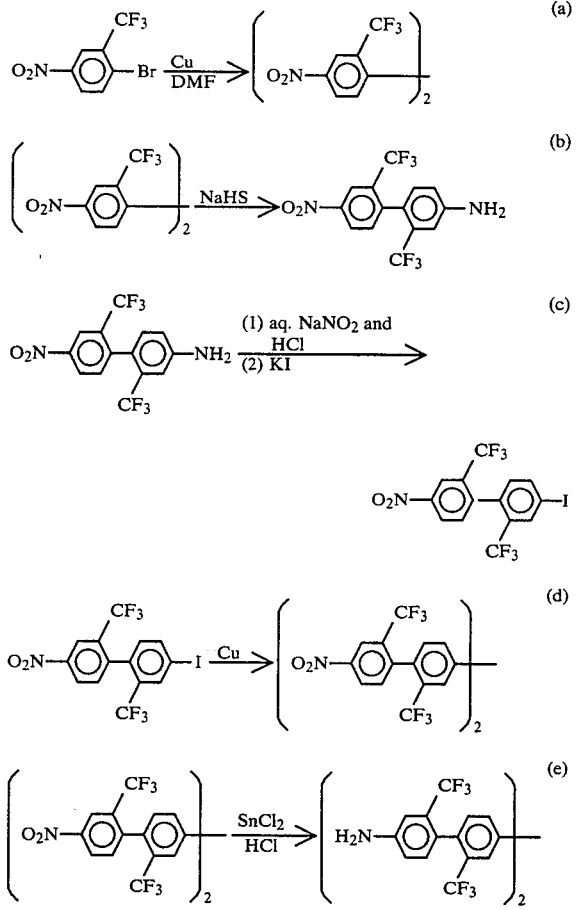

The substituted-quaterphenylene polyamides of the present invention can be variously formed or shaped into films, sheets, coatings, layers, fibrils, fibers or the like. For example, a solution of a substituted polyamide as described hereinbefore, in a solvent material such as N,N-dimethylacetamide, optionally containing lithium chloride solubilizing agent, can be readily cast onto a suitable support material for the formation of a polymeric film or layer of the polyamide material. The polymeric film can be utilized for the production of a birefringent polymeric film or sheet material which can be utilized in various optical devices. Thus, a polymeric film or sheet material can be subjected to stretching so as to introduce molecular orientation and provide a film material having a highly birefringent character.

The substituted-quaterphenylene polyamides of the present invention can also be formed into fibers, fibrils or the like by extrusion or spinning methods known in the art. Thus, for example, a solution of the substituted-quaterphenylene polyamide, in a solution such as N,N-dimethylacetamide containing lithium chloride, can be extruded or spun into a coagulating bath for coagulation of the polymeric material into the form of fibers which can be cut, stretched or assembled into fiber tows or bundles as desired. The fibers, fibrils, tows or the like can be washed for removal of residual solubilizing agents, solvents, extruding or spinning aids and dried to materials exhibiting birefringent properties.

The substituted-quaterphenylene polyamides of the present invention are especially advantageous from the standpoint of the provision of materials exhibiting high birefringence. These polyamides, as prepared and in solution in a suitable reaction solvent, exist in an unoriented and non-birefringent form. The substituted-quaterphenylene polyamides respond, however, to stress and exhibit birefringent character. Thus, solutions of the polyamides hereof, upon the application of slight stress, exhibit streaming birefringence, which can be observed by placement of the stressed material between crossed polarizers and observation of the transmission of light therethrough as the result of depolarization of light by the stressed birefringent material. The property of streaming birefringence observed in this manner with the aid of crossed polarizers is not visually detected by inspection of the clear, transparent polymer solution and is to be distinguished from the stress-induced satin-like sheen or pearlescence characteristic of materials exhibiting stir opalescence. The streaming birefringence exhibited by the substituted-quaterphenylene polyamides hereof (upon the application of stress) will normally be rapidly extinguished upon relaxation of the stress. Where a molecular orientation is permanently induced in the polyamide material, as by formation of the polyamide material into an oriented sheet, fiber or other form, the polyamide will exhibit optical birefringence which can be measured in accordance with a number of known methods.

Known shaping of forming methods can be utilized for the orientation of polymeric materials of the present invention. Preferably, this will be accomplished by unidirectional stretching of a polymeric film, by extrusion of the polymer into a sheet, layer or other stretched form, or by the combined effects of extrusion and stretching. In their oriented state, the polymers of the invention exhibit unusually high birefringence. In general, greater birefringence will be observed in the case of polymeric materials exhibiting a greater degree of molecular orientation. It will be appreciated, however, as has been pointed out hereinbefore, that the particular molecular structure or configuration of the polymeric material may affect desired physcial attributes of the polymer material or otherwise impose a practical limitation upon the degree of orientation that can be realized by stretching or other means. It is a significant aspect of the present invention, however, that the. substituted-quaterphenylene polyamides of the present invention, particularly for a given degree of orientation, exhibit unusually high birefringence.

The birefringent polymeric materials of the present invention, in addition to exhibiting high birefringent properties, are advantageous from the standpoint of their transparency. In contrast to polymeric materials which become decidedly opaque as a result of stretching, the birefringent materials hereof exhibit optical transparency in unoriented and stretched forms. For example, the substituted-quaterphenylene polyamides described herein exhibit a high transparency and a low order of light scattering, exhibiting a ratio of amorphous to crystalline material of from about 10:1 to about 20:1 by weight. These materials are, thus, suited to optical applications where a light-transmissive, highly refractive and birefringent material is desirably utilized. Depending upon the nature of substituent moieties on the divalent radicals of the recurring units of these polyamides, colorless or nearly colorless polymeric films or layers can be fabricated. Where, for example, nitro-substituted quaterphenylene radicals are present, a yellow transparent film or fiber can be fabricated.

The substituted-quaterphenylene polyamides of the present invention are especially advantageous from the standpoint of their solubility in such non-amide solvents as acetone; lower alkanols such as ethanol; and ethers such as diethylether, 2-methoxy-1-ethanol and 2-ethoxy-1-ethanol. In addition to conferring a condition of non-coplanarity, the presence of substituent groups on the interbonded phenylene moieties of the polyamides of the invention, is believed to promote solubility of the polyamides in certain solvent materials. Thus, the substituted-quaterphenylene polyamides of the invention ae soluble in solvents of the amide-type, such as N-methyl-pyrrolidone and N,N,N',N'-tetramethylurea and in non-amide type solvents as mentioned hereinbefore. The improved solubility of the substituted-quaterphenylene polyamides of the invention, relative to polyamides in general, permits improved handling of the polymers and facilitates the production of polymeric layers formed to the desired shape or conformation suited to particular applications. Films and coated or other shaped forms of the substituted-quaterphenylene polyamides can be redissolved and reshaped or refabricated if desired. Depending upon the nature of particular recurring units of the polyamide materials, and particularly the nature of substituent moieties and solvent materials, the solubility characteristics of these substituted polyamides can be varied or controlled to suit particular applications.

The birefringent properties of polymers of the present invention can be determined by the measurement of physical and optical parameters in accordance with known principles of physics and optics. Thus, for example, the birefringence ($\Delta n$) of a suitable birefringent polymeric material can be determined by the measurement of optical phase retardation (R) and film thickness (d) and calculation of birefringence in accordance with the relationship $$\Delta n = (R\lambda/d)$$

where $\lambda$ represents the wavelength of light utilized for the conduct of the measurements. Alternatively, parallel refractive index and perpendicular refractive index of the film material can be measured utilizing Becke line analysis of critical angle measurement.

A preferred method for determining the birefringence of polymers of the invention involves the measurement of retardation of the polymeric material by a method utilizing principles of polarized-light microscopy and interferometry. Such method provides desired precision and accuracy in the measurement of the phase difference between a sample ray passing through a sample of polymeric material and a reference ray passing through a neighboring empty area (embedding medium or air) of the same thickness. The light emitted by a low-voltage lamp of a microscope is linearly polarized by passage through a polarizer and, in turn, is passed through a condenser, a calcite plate beam splitter, a half-wave retarder plate, the polymeric sample, a beam recombinator calcite plate, and through an analyzer whose transmission direction is vertical to that of the polarizer (crossed position). In the analyzer the components vibrating in its absorption direction are extinguished, whereas the components of both rays in the transmission direction are transmitted and interfere. The phase difference between sample and reference beams, caused by the molecular structure or configuration of the polymeric sample, is measured with compensators. From these measurements, the thickness and refractive index of the polymeric material can be determined. By determining index of refraction of the polymeric sample for both parallel and perpendicular directions, birefringence can, by difference, be determined. A suitable method and apparatus for determining phase retardation, index of refraction and birefringence for the polymeric materials utilized herein is a pol-interference device according to Jamin-Lebedeff described in greater detail by W. J. Patzelt "Polarized-light Microscopy", Ernest Leitz GmbH, Wetzlar, West Germany, 1974, page 92.

The substituted-quaterphenylene polyamides of the present invention can be utilized in the construction of a variety of optical filter or other devices. In general, such devices are multilayer devices which include a layer of molecularly oriented and birefringent polymeric material and, in addition, at least one other layer of isotropic or birefringent material. The substituted-quaterphenylene polyamides of the invention exhibit high birefringence and be suitably employed in the construction of such devices. The additional layer or layers of such devices, whether isotropic or birefringent, will generally comprise materials having an index of refraction matching substantially one index of refraction of the highly birefringent polymeric material of the invention. For example, a layer of isotropic material having an index of refraction matching substantially one index of refraction of the highly birefringent layer can be suitably bonded to the layer of highly birefringent polymer. A preferred device comprises a layer of the molecularly oriented and highly birefringent material of the invention bonded between two layers of isotropic material, the index of refraction of each isotropic layer constituting substantially a match with an index of refraction of the molecularly oriented and highly birefringent material. Such a preferred device can be utilized for the polarization of light and may be termed a "total transmission" light polarizer, i.e., one which is particularly adapted to polarize a very large portion of incident light. Total polarizers find application in equipment such as may be employed for signaling, projection and display purposes, or the like, and in antiglare systems for automotive vehicles.

According to another application of the polymeric materials of the present invention, a plurality of alternating isotropic and birefringent layers can be utilized for the production of a multilayer light polarizing device, at least one of the layers of birefringent material comprising a molecularly oriented and highly birefringent material as defined herein. Such a device can be utilized as a multilayer polarizer which partly transmits and partly reflects incident light as separate linearly polarized components vibrating in orthogonal directions.

Optical devices in which the substituted-quaterphenylene polyamides of the invention can be utilized, and their methods for construction and modes of operation are described in detail in U.S. Pat. application of H. G. Rogers et al., Ser. No. 238,054, issued May 1, 1984 as U.S. Pat. No. 4,446,305. Examples of other devices which can be adapted to include a polymeric and highly birefringent layer as described herein are described, for example, in U.S. Pat. No. 3,506,333 (issued Apr. 14, 1970 to E. H. Land; in U.S. Pat. No. 3,213,753 (issued Oct. 26, 1965 to H. G. Rogers); in U.S. Pat. No. 3,610,729 (issued Oct. 5, 1971 to H. G. Rogers); in U.S. Pat. No. 3,473,013 (issued Oct. 14, 1969 to H. G. Rogers); in U.S. Pat. No. 3,522,984 (issued Aug. 4, 1970 to H. G. Rogers); in U.S. Pat. No. 3,522,985 (issued Aug. 4, 1970 to H. G. Rogers); in U.S. Pat. No. 3,528,723 (issued Sept. 15, 1970 to H. G. Rogers); and in U.S. Pat. No. 3,582,424 (issued June 1, 1971 to K. Norvaisa).

The following non-limiting examples are illustrative of the present invention.

EXAMPLE 1

This example illustrates the preparation of poly[2,2',-3'',2'''-tetrakis(trifluoromethyl)-1,1':4',1'':4'',1''':4'''-quaterphenylene]-trans-p,p'-stilbenedicarboxamide and the preparation therefrom of birefringent polymeric films.

A 100-ml. reaction vessel (a resin-making kettle equipped with a mechanical stirrer, nitrogen inlet tube and calcium chloride drying tube) was heated while simultaneously flushing the vessel with nitrogen. After the reaction vessel had cooled to room temperature, 1.5 grams of anhydrous lithium chloride and 0.5806 gram (0.0009543 mole) of recrystallized 4,4'''-diamino-2,2',3'',2'''-tetrakis(trifluoromethyl)-1,1':4',1'':4'',1'''-quaterphenyl were added while maintaining a positive nitrogen pressure. The reaction vessel was fitted with a thermometer and a rubber stopple (a rubber membrane-like sealing lid capable of receiving a syringe and of sealing itself upon removal of the syringe). Ten mls. of anhydrous distilled tetramethylurea (TMU) were carefully added with the aid of syringes. The resulting mixture was stirred and warmed to 40° C. until all solids had dissolved. The solution was then cooled in a bath of ice and salt to a temperature of $-5°$ C. A small amount of lithium chloride precipitation was observed. Recrystallized trans-p,p'-stilbene dicarbonyl chloride (0.2909 gram; 0.0009543 mole) was carefully added by means of a funnel to the stirred diaminoquaterphenyl solution. An additional 10 mls. of TMU, at a temperature of 0° C., were added through the funnel to the reaction mixture. The temperature of the reaction mixture did not rise above a temperature of 7° C. and then dropped rapidly to 0° C. After stirring for 30 minutes, the reaction mixture began to thicken and streaming birefringence (but not stir opalescence) was observed. Stirring was continued for an additional 30 minutes at 0° C.

The ice bath was removed from the reaction vessel, and when the temperature reached 20° C. (in 30 minutes), the reaction solution had become very viscous. Over the next 75 minutes, the light yellow, opaque solution was warmed to 45° C. After stirring at this temperature for the next 18 hours, the transparent polymer solution was poured into 200 mls. of ice and water in a blender. The resulting fibrous solid was filtered and washed (in the blender) twice each with water and ether. The product was dried in a vacuum oven at 15 mm. pressure and 90° C. for 18 hours. The polymeric product, obtained in 92.2% yield, was a very light-yellow fibrous solid having the following recurring structural units:

The inherent viscosity of a polymer solution (0.5 gram of the polymer of this Example per 100 mls. of a solution of five grams lithium chloride per 100 mls. of dimethylacetamide) was 1.31 dl./gram at 30° C. The molecular structure of the polymer was confirmed by infrared spectroscopy. The polymer was soluble in tetrahydrofuran, in acetone and in various amidetype solvents, with and without added lithium chloride.

Elemental analysis for $C_{44}H_{24}F_{12}N_2O_2$ provided the following:

|  | % C | % H | % F | % N | % O |  |
|---|---|---|---|---|---|---|
| Calculated: | 62.86 | 2.88 | 27.12 | 3.33 | 3.81 |  |
| Found: | 62.07 | 3.29 | 24.18 | 3.16 | 7.3 | (by difference) |

Thermogravimetric analysis showed that the onset of degradation of the polymer of this Example occured at 510° C. in nitrogen and at 440° C. in air. Differential scanning calorimetry and thermal mechanical analysis of film samples detected a reproducible transition at about 187° C.

Polymeric films were prepared from the polymeric material of Example 1 by casting (onto glass plates) solutions of the polymeric material in a 5% wt./vol. solution of lithium chloride and dimethylacetamide (five grams lithium chloride per 100 mls. of dimethylacetamide). The concentration of polymer ranged from 1.0 to 5% wt./vol., i.e., from 1.0 gram to five gramps polymer per 100 mls. of the lithium chloride/dimethylacetamide solution. In each instance, the glass plate carrying the puddle-cast polymer solution was immersed in water (after minimal evaporation of solvent). The polymer film was observed to gel and a transparent and colorless unoriented film separated from the glass plate. The resulting film was soaked for several hours in water to effect extraction of occluded lithium chloride and solvent, soaked in acetone and dried in a vacuum oven at 90° C. and 15 mm. pressure. Refractive index, measured by interferometry, was 1.810.

Stretched polymeric films were prepared in the following manner. Water-swollen films (obtained by soaking the polymer films for several hours for removal of occluded lithium chloride and solvent as aforedescribed) were cut into strips. The strips were mounted between the jaws of a mechanical unidirectional stretcher. The strips were stretched in methanol and then in air at 220° C. to effect film orientation. The stretched films were optically transparent. Birefringence, measured with the aid of a quartz wedge, was 0.87.

EXAMPLE 2

This example illustrates the preparation of poly[2,2',-3'',2'''-tetrakis(trifluoromethyl)-1,1':4',1'':4'',1''':4'''-quaterphenylene]terephthalamide and the preparation therefrom of birefringent polymeric films.

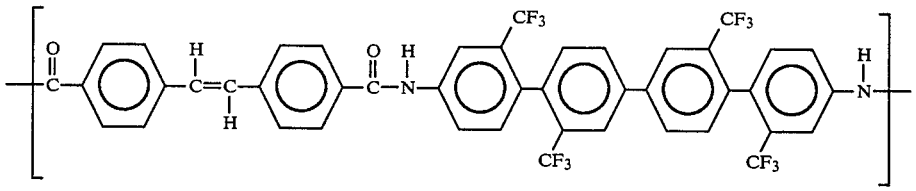

A 100-ml. reaction vessel (a resin-making kettle equipped with a mechanical stirrer, nitrogen inlet tube and calcium chloride drying tube) was heated while simultaneously flushing the vessel with nitrogen. After the reaction vessel had cooled to room temperature, 1.5 grams of anhydrous lithium chloride and 0.6301 gram (0.001036 mole) of recrystallized 4,4'''-diamino-2,2',3'',2'''-tetrakis(trifluoromethyl)-1,1':4',1'':4'',1'''-quaterphenyl were added while maintaining a positive nitrogen pressure. The reaction vessel was fitted with a thermometer and a rubber stopple and ten mls. of anhydrous distilled N-methylpyrrolidone (NMP) and ten mls. of anhydrous distilled tetramethylurea (TMU) were carefully added with the aid of syringes. The resulting mixture was stirred and warmed to 40° C. until all solids had dissolved. The solution was then cooled in a bath of ice and salt to a temperature of +5° C. A small amount of lithium chloride precipitation was observed. Recrystallized terephthaloylchloride (0.2103 gram; 0.001036 mole) was carefully added by means of a funnel to the stirred 2,2'-diaminoquaterphenyl solution. An additional 10 mls. of TMU, at a temperature of 10° C., were added through the funnel to the reaction mixture. The temperature of the reaction mixture did not rise above a temperature of 10° C. and then dropped to 15° C. After stirring for 30 minutes, the reaction mixture began to thicken and streaming birefringence (but not stir opalescence) was observed. Stirring was continued for an additional 30 minutes at 10° C.

The ice bath was removed from the reaction vessel, and when the temperature reached 27° C. (in 30 minutes), the reaction solution had become very viscous. Over the next 75 minutes, the light yellow, transparent solution was warmed to 40° C. After stirring at this temperature for the next 18 hours, the polymer solution was poured into 200 mls. of ice and water in a blender. The resulting fibrous solid was filtered and washed (in the blender) twice each with water and ether. The product was dried in a vacuum oven at 15 mm. pressure and 90° C. for 18 hours. The polymeric product, obtained in 93.5% yield, was a white fibrous solid having the following recurring structural units:

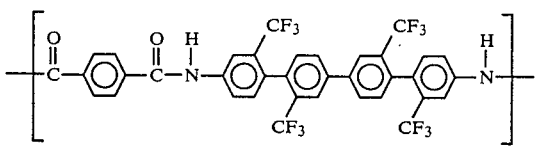

The inherent viscosity of a polymer solution (0.5 gram of the polymer of this Example per 100 mls. of a solution of five grams lithium chloride per 100 mls. of dimethylacetamide) was 6.55 dl./gram at 30° C. The molecular structure of the polymer was confirmed by infrared spectroscopy. The polymer was very slightly soluble in acetone, in tetrahydrofuran and in ethyl acetate and was soluble in amide-type solvents with or without added lithium chloride.

Elemental analysis for $C_{36}H_{18}F_{12}N_2O_2$ provided the following:

|  | % C | % H | % F | % N | % O |  |
| --- | --- | --- | --- | --- | --- | --- |
| Calculated: | 58.23 | 2.44 | 30.71 | 3.77 | 4.85 |  |
| Found: | 57.87 | 2.50 | 30.56 | 3.77 | 5.3 | (by difference) |

Thermogravimetric analysis showed that the onset of degradation of the polymer of this Example occurred at 440° C. in nitrogen and in air. Differential scanning calorimetry and thermal mechanical analysis of film samples detected a reproducible transition at about 160° C.

Polymeric films were prepared from the polymeric material of Example by casting (onto glass plates) solutions of the polymeric material in a 5% wt./vol. solution of lithium chloride and dimethylacetamide (five grams lithium chloride per 100 mls. of dimethylacetamide). The concentration of polymer ranged from 1.0 to 5% wt./vol., i.e., from 1.0 gram to five gramps polymer per 100 mls. of the lithium chloride/dimethylacetamide solution. In each instance, the glass plate carrying the puddle-cast polymer solution was immersed in water (after minimal evaporation of solvent). The polymer film was observed to gel and a transparent and colorless unoriented film separated from the glass plate. The resulting film was soaked for several hours in water to effect extraction of occluded lithium chloride and solvent, soaked in acetone and dried in a vacuum oven at 90° C. and 15 mm. pressure. Refractive index, measured by interferometry, was 1.790.

Stretched polymeric films were prepared in the following manner. Water-swollen films (obtained by soaking the polymer films for several hours for removal of occluded lithium chloride and solvent as aforedescribed) were cut into strips. The strips were mounted between the jaws of a mechanical unidirectional stretcher. The strips were stretched (in air at 220° C.) to effect film orientation. The stretched films were optically transparent. Birefringence, measured with the aid of a quartz wedge, was 0.293.

Solutions of the polymer of this Example in lithium chloride/dimethylacetamide, as aforedescribed, were formed into extruded films by the "wet-jet" method whereby the solution of polymer is extruded into an aqueous coagulation bath for gelling of the polymer material. The resulting transparent colorless film strips were soaked in water and cut to about 1 to 2 inches (25.4 to 50.8 mm.) for testing. The partially oriented strips of film produced by the extrusion were further oriented by stretching in the manner described in the Examples hereof. Measurement of birefringence utilizing a quartz wedge provided a birefringence value of 0.44.

EXAMPLE 3

For purposes of comparison with the substituted-quaterphenylene polyamides of the present invention, an unsubstituted polyamide was prepared and evaluated in the following manner.

A solution polymerization reaction for the production of poly(p-benzamide) was conducted in accordance with the following reaction scheme:

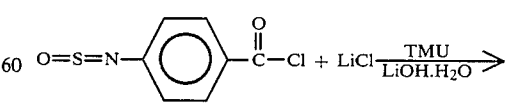

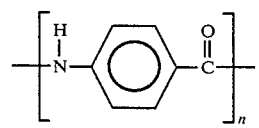

A 50-ml. reaction vessel (a resin-making kettle equipped with mechanical stirrer, nitrogen inlet tube and calcium chloride drying tube) was heated while simultaneously flushing the vessel with nitrogen. After the reaction vessel had cooled to room temperature, 40 mls. of anhydrous distilled tetramethyl urea (TMU), 8.04 grams (0.04 mole) of vacuum-distilled p-thionylaminobenzoyl chloride and 0.52 gram (0.012 mole) of lithium chloride were added while maintaining a positive nitrogen pressure. The resulting reaction mixture was stirred for ten minutes at room temperature and 1.68 grams (0.04 mole) of lithium hydroxide monohydrate were added while vigorously stirring. The reaction mixture was then stirred for one hour at room temperature. After a period of seven additional minutes, the reaction mixture became cloudy and was observed to thicken. The polymeric reaction product, after 20 minutes, thickened sufficiently to adhere the shaft of the mechanical stirrer. After one-half hour, the reaction mixture, which could not be stirred, was heated. An additional quantity (14 mls.) of TMU was added at which point the reaction mixture still could not be stirred. The reaction mixture was then heated to 130° C. without stirring. After two hours of heating at 130° C., pliability of polymeric reaction mass increased and the product appeared to have partially dissolved. The reaction product was stored in the reaction vessel overnight and was washed with water, filtered and washed with acetone, then ether. The product, poly(p-benzamide) was dried in a vacuum oven at 80° C. for two hours.

The inherent viscosity of a polymer solution of poly(p-benzamide) in sulfuric acid was 1.60 dl./gram at 30° C.

Polymeric films of poly(p-benzamide) were prepared by casting a solution of the polymeric material in a 5% wt./vol. solution of lithium chloride and dimethylacetamide (five grams polymer per 100 mls. of the lithium chloride/dimethylacetamide solution. The case polymer film was dried in a vacuum oven at 90° C. (30 in. Hg) overnight. The polymer film was an opaque, white flexible film. Additional films were formed by puddle-casting the solution as aforedescribed onto glass plates. In each instance, the glass plate carrying the puddle-case polymer solution was immersed in water (after most of the solvent had evaporated). The polymer film which separated from the glass plate was a tough, transparent, flexible film. The resulting film was soaked for several hours in water to effect extraction of occluded lithium chloride and solvent.

Stretched polymeric films were prepared in the following manner. Water-swollen films (obtained by soaking the polymer films for several hours for removal of occluded lithium chloride and solvent as aforedescribed) were cut into strips. The strips were mounted between the jaws of a mechanical stretcher and were unidirectionally stretched, successively, in steam and in air (at 200° C.). The strips were stretched to an elongation of approximately 10%. The resulting stretched films were clouded in appearance. Optical retardation was measured with a calibrated quartz wedge; film thickness was measured with a micrometer. Birefringence, measured by means of a quartz wedge, was 0.23.

EXAMPLE 4

Geometric indices were determined for the repeating units of polymeric materials having the following structure

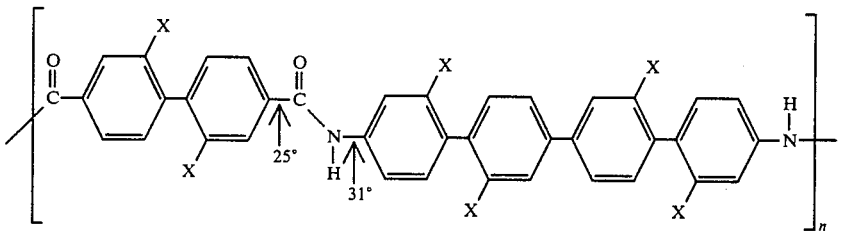

wherein each X is hydrogen or a substituent as set forth in the following Table I. In the case of each recurring unit, the eccentricity factor $(1+e_L)/(1+e_T)$ was calculated and is reported in Table I. Bond and group polarizability tensors were utilized to calculate a polarizability matrix for each repeat unit, the diagonalized form of the matrix providing the X, Y and Z contributions to the unit polarizability ellipsoid. Axial polarizabilities, i.e., X, Y and Z, were utilized to calculate longitudinal and transverse eccentricities of each repeat unit, thus, reflecting its symmetry.

Eccentricity values were calculated utilizing the following procedure. A polarizability and a corresponding orthogonal coordinate system is assigned to each segment of the polymer repeat unit. Literature values for group polarizabilities are utilized from the literature, or where not available, are constructed from bond polarizabilities. Available Denbigh values were utilized herein for all calculations. Bond polarizabilities are utilized to connect segments where necessary. To determine the overall polarizability of the repeat unit, the coordinate system of the segment at one end of the repeat unit is made coincident with that of the adjacent segment by means of the appropriate rotation(s). This procedure is repeated on each successive segment until the last segment is reached. Mathematically, this means that the matrix of one segment must be pre- and post-multiplied by a transformation matrix:

$$\alpha_1' = \underline{Y} \alpha_1 Y^{-1}$$

where $\alpha_1$ is the polarizability of segment 1; Y is the transformation matrix; $Y^{-1}$ is the inverse of Y; and $\alpha_1'$ is the polarizability of segment 1 in the coordinate system of segment 2. The value of $\alpha_1'$ is then added to $\alpha_2$ and the transformation repeated. The repeat unit polarizability matrix is diagonalized, thus, providing a repeat unit polarizability ellipsoid with three semi-axes, i.e., $\alpha_{xx}$, $\alpha_{yy}$, and $\alpha_{zz}$, where $\alpha_{xx}$ is the major polarizability and is coincident with the polymer backbone.

Literature-reported values of 25° and 31°, respectively, were utilized in all calculations as representing the dihedral angle between the phenyl and carbonyl moieties and the dihedral angle between the phenyl and amino moieties, respectively. Experimentally determined values for the dihedral angle between each X- substituted phenyl moiety were utilized in all calculations and are reported in Table I. Mean diameter values, D, and length, L, were obtained from space-filling molecular models.

TABLE I

| Substituent X (Dihedral Angle) | Mean Diameter (D) | Length (L) | $\left(\dfrac{1+e_L}{1+e_T}\right)$ | G |
|---|---|---|---|---|
| H (20°)    | 4.52 | 29.80 | 0.938 | 1.373 |
| F (60°)    | 4.66 | 29.80 | 1.155 | 1.640 |
| Cl (72°)   | 4.84 | 29.80 | 1.166 | 1.594 |
| Br (75°)   | 4.90 | 29.80 | 1.145 | 1.546 |
| I (85°)    | 4.99 | 29.80 | 1.271 | 1.685 |
| CF$_3$ (80°) | 4.98 | 29.80 | 1.286 | 1.708 |
| CH$_3$ (71°) | 4.82 | 29.80 | 1.181 | 1.621 |

From the data presented in Table I will be observed the influence of the nature of the X substituent relative to a hydrogen atom as regards the reported dihedral angle and resulting substantial noncoplanarity between interbonded phenyl rings. Differences in mean diameter and influence of the nature of X substituents on mean diameter and eccentricity factor, and correspondingly, geometric index G will also be observed. Thus, it will be noted that the largest substituents, i.e., —CF$_3$ and —I substituents, corresponded with the largest dihedral angles between interbonded phenyl groups or the highest non-coplanarity and, accordingly, recurring units having such substituents show high geometric index values.

For purposes of comparison, geometric index G was calculated for the repeat unit of poly(p-phenylene)-terephthalamide having the following structure and the results thereof are reported in Table II. Dihedral angle values of 25° and 31° were utilized for purposes of calculation as in the case of the repeat units of Example 4.

TABLE II

[structural formula of poly(p-phenylene terephthalamide) repeat unit with 25° and 31° dihedral angles shown]

| Mean Diameter (D) | Length (L) | $\dfrac{1+e_L}{1+e_T}$ | G |
|---|---|---|---|
| 4.43 | 12.45 | 0.978 | 0.621 |

As can be observed from inspection of the data reported in Tables I and II, the geometric indices for the repeat units of the materials set forth in Table I are considerably higher than the geometric index calculated for poly(p-phenylene)terephthalamide of Table II.

The enhanced optical anisotropy exhibited by the substituted quaterphenylene polyamide materials hereof is believed to be the result of the rigid, rod-like uniaxial molecular structure of such materials and the amorphous/crystalline ratio thereof. This ratio typically ranges from about 10:1 to about 20:1. In the case of highly unidirectionally oriented phenyl-type polyamides this ratio generally will be in the range of about 0.3:1. The presence of crystallites is generally detrimental in polymeric materials adapted to utilization in optical devices owing to light scattering and diminished transparency. The non-coplanarity between substituted quaterphenyl rings, resulting from sterically bulky groups on the ortho positions of interbonded phenyl rings, raises the amorphous/crystalline ratio to the range of about 10:1 to about 20:1. This permits the fabrication of highly oriented films and fibers exhibiting high transparency in addition to high birefringence. The ring-substituted quaterphenyl polyamides additionally exhibit enhanced solubility and can be fabricated into colorless films or fibers where desired.

EXAMPLE 5

This Example illustrates the preparation, in accordance with the reaction sequence set forth hereinbefore, of 4,4'''-dinitro-2,2',3'',2'''-tetrakis-(trifluoromethyl)-1,1':4',1'':4'',1'''-quaterphenyl and the corresponding diamino compound.

Part A.—Preparation of 2,2'-bis(trifluoromethyl)-4,4'-dinitro-1,1'-biphenyl

To a solution of 2-bromo-5-nitro-benzotrifluoride (50 grams) in 100 mls. of dimethylformamide were added 45 grams of activated copper and the mixture was refluxed for five hours. The reaction mixture was cooled and poured into excess water. The product, a brown precipitate, was filtered off, washed with water and dried. Chromatography over silica gel provided the product 2,2'-bis-(trifluoromethyl)-4,4'-dinitro-1,1'-biphenyl which was recrystallized from ether as shiny yellow prisms exhibiting a melting point of 140° C.

Part B.—Preparation of 4-amino-2,2'-bis-(trifluoromethyl)-4'-nitro-1,1'-biphenyl In 50 mls. of methanol and 75 mls. of toluene, 4.75 grams of the product from Part A were dissolved. The solution was refluxed while a solution (2.1 grams of sodium hydrosulfide in 50 mls. of water and 50 mls. of methanol) was added dropwise over a 45-minute period. As shown by thin layer chromatography, the reaction was completed 150 minutes after the addition. The reaction solvents were removed in vacuo. Water (100 mls.) was added to the residue, and then extracted with ethyl acetate. The organic layers were washed with water, dried (Na$_2$SO$_4$) and solvent removed to provide a yellow syrup-like liquid. Thin layer chromatography showed a trace of the corresponding diamine compound in the resulting product which was utilized without purification in Part C as follows.

Part C—Preparation of 2,2'-bis-(trifluoromethyl)-4-iodo-4'-nitro-1,1'-biphenyl

The product from Part B (4.5 grams) was diazotized with sodium nitrite and hydrochloric acid and the diazonium salt solution was added slowly to a stirring solution of potassium iodide (5 grams), iodine (1 gram) and water (10 mls.) maintained at 0° C. The temperature was allowed to rise to room temperature and the reaction mixture was stirred for one-half hour and then heated over a steam bath for one hour. The reaction mixture was cooled, diluted with water, excess iodine was destroyed by adding sodium bisulfite and extracted with ethyl acetate. The ethyl acetate layers were washed with aqueous sodium bisulfite and water, dried (Na$_2$SO$_4$) and evaporated to provide a yellow low-melting solid. This was absorbed on dry column silica gel. Elution with benzene/hexane (½) gave 4.2 grams of 2,2'-bis-(trifluoromethyl)-4-iodo-4'-nitro-1,1'-biphenyl and 0.15 gram of the di-iodo compound. The desired compound was crystallized as a pale yellow solid from methanol and exhibited a melting point of 67°–68° C.

Part D.—Preparation of 4,4'''-dinitro-2,2',3'',2'''-tetrakis(trifluoromethyl)-1,1':4',1'':4'',1'''-quaterphenyl Nine grams of the compound from Part C were dissolved in 20 mls. of dimethylformamide. Nine grams of activated copper were added and the reaction mixture was refluxed under nitrogen for 30 hours. The mixture was poured into water, the brown precipitate was filtered off, washed with water and dried. It was extracted overnight in a Soxhlet extractor with acetone and the acetone solution was evaporated to provide a yellow residue. Chromatography over dry column silica gel and elution with benzene/hexane (1/1) gave a white solid, crystallized as short white needles from chloroform/methanol and exhibiting a melting point of 250°–255° C.

Part E.—Preparation of 4,4'''-diamino-2,2',3'',2'''-tetrakis(trifluoromethyl)-1,1':4',1'':4'',1'''-quaterphenyl The compound from Part D hereof (4 grams) was well mixed with 11 grams of SnCl$_2$.2H$_2$O to which absolute ethanol (10 mls.) was added and stirred while concentrated hydrochloric acid (15 mls.) was dropped in carefully. The mixture was refluxed overnight, ethanol was removed, water was added to the residue and then made basic with 20% sodium hydroxide. The white precipitate was filtered off, dried and extracted overnight in a Soxhlet extractor with ethyl acetate. Removal of solvent and recrystallization of the residue from chloroform/hexane gave the desired diamine compound as short white needles exhibiting a melting point of 208°–210° C.

Elemental analysis for C$_{28}$H$_{16}$F$_{12}$N$_2$ provided the following

|  | % C | % H | % N | % O |
|---|---|---|---|---|
| Calculated: | 55.3 | 2.6 | 4.6 | 37.5 |
| Found: | 55.4 | 2.7 | 4.6 | 37.4 |

What is claimed is:
1. A compound having the formula

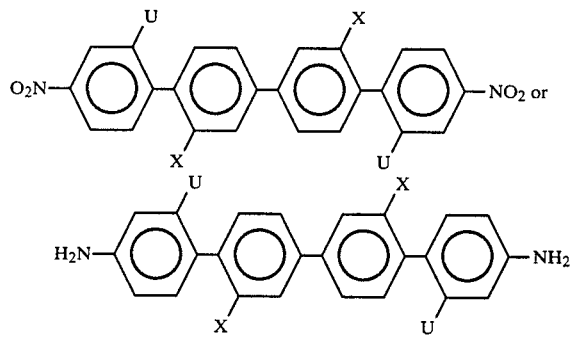

wherein each of U and X is halo; alkoxy; or trifluoromethyl.

2. The compound of claim 1 having the formula

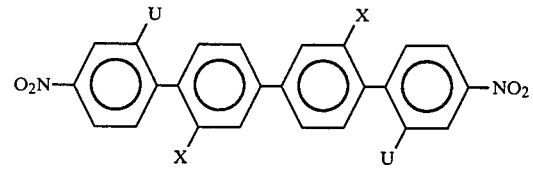

wherein each of U and X is trifluoromethyl.

3. The compound of claim 1 having the formula

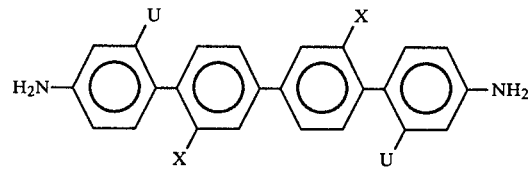

wherein each of U and X is trifluoromethyl.

* * * * *